United States Patent
Mello et al.

(12) 
(10) Patent No.: US 6,271,216 B1
(45) Date of Patent: Aug. 7, 2001

(54) STABLE SOLUTION OF HYALURONATE IN A BALANCED SALT MEDIUM

(75) Inventors: Robert J. Mello; William P. Tew, both of Baltimore; Narlin B. Beaty, Cockeysville, all of MD (US)

(73) Assignee: Allergan, Waco, TX (US)

( * ) Notice: Subject to any disclaimer, the term of this patent is extended or adjusted under 35 U.S.C. 154(b) by 0 days.

(21) Appl. No.: 07/912,029

(22) Filed: Jul. 9, 1992

Related U.S. Application Data

(63) Continuation of application No. 07/798,835, filed on Nov. 25, 1991, now abandoned, which is a continuation of application No. 07/542,389, filed on Jun. 23, 1990, now abandoned, which is a continuation-in-part of application No. 07/384,530, filed on Jul. 24, 1989, now abandoned.

(51) Int. Cl.$^7$ .................. A61K 31/685; A61K 31/715
(52) U.S. Cl. .................. 514/78.04; 514/912; 514/54; 424/678; 424/681
(58) Field of Search .................. 424/678, 681; 514/54, 912, 78.04

(56) References Cited

U.S. PATENT DOCUMENTS

| | | |
|---|---|---|
| 4,141,973 | 2/1979 | Balazs . |
| 4,303,676 | 12/1981 | Balazs . |
| 4,517,295 | 5/1985 | Bracke et al. . |
| 4,696,917 | 9/1987 | Lindstrom et al. . |
| 4,725,586 | 2/1988 | Lindstrom et al. . |
| 4,886,786 | 12/1989 | Lindstrom et al. . |

FOREIGN PATENT DOCUMENTS

| | | |
|---|---|---|
| 3080684 | 10/1986 | (AU) . |
| 62122671 | 6/1989 | (JP) . |

OTHER PUBLICATIONS

Derwent Abst: C87–081037 (Mar. 6, 1987).*
Derwent Abstract of JP62122671, Mar. 1987.*
VITRAX, Formulation Package Insert, Weck Feb. 1989.
American Journal of Opthal., 99, Mar. 1985, p. 322.
Chang et al, Abstract, Chondroitin Sulfate/Sodium Hyaluronate Compositions, EP–136782 (1985).
Miyama, Abstract, Cosmetic Compositions Containing Mineral Components 86JP–0182693 (1988).
Ocular Surgery News, Aug., 1987, pp. 44–47.
Package Insert for Healon.
Package Inwert for AMVISC.
Package Insert for VISCOAT.
Denlinger, J.L., et al, "Replacement of the Liquid Vitreus with Sodium Hyaluronate in Monkeys," Exp. Eye Res. (1980) 31, 81–99,101–117.
1988 PDR for Ophthalmology—Alcon Labs balanced salt solution.
Edelhauser, H.F., Van Horn, D.L., Hyndiuk, R.A., Schultz, R.O., "Intraocular Irrigating Solution: Their Effect on the Corneal Endothelium," ARch. Ophthalmol., 93: 648, 1975.
Edelhauser, H.F., Van Horn, D.L., Schultz, R.O., Hyndiuk, R.A., "Comparative Toxicity of Intraocular Irrigating Solution on the Corneal Endothelium," Am. J. Ophthalmol., 81; 473, 1976.
Moorhead, L.C., Redburn, D.A., Merritt, J., Garcia, C.A., "The Effects of Intravitreal Irrigation During Vitrectomy on the Electroretinogram," Am. J. Ophthalmol., 88: 239, 1979.
McCulley et al, A New Quantitative Method for the In Vitro Assessment of Experimental and Clinical Sodium Hyaluronate (SH) Preparations, ARVO Abstract volume, Mar. 1989, vol. 30, No. 3.

* cited by examiner

Primary Examiner—Zohreh Fay
(74) Attorney, Agent, or Firm—Stout, Uxa, Buyan & Mullins; Frank J. Uxa

(57) ABSTRACT

A stable physiologic balanced salt solution of a hyaluronate salt, such as sodium hyaluronate, is provided which contains calcium ion, for example, in the form of calcium chloride or calcium acetate, and magnesium ion, for example in the form of magnesium chloride or magnesium acetate, together with sodium chloride, potassium chloride or potassium acetate, sodium acetate, sodium citrate and water, and optionally bicarbonate, dextrose and glutathione disulfide, preservatives and other conventional ingredients employed in irrigating solutions. This solution is used as a visco-elastic ophthalmic device during ophthalmic surgery.

19 Claims, No Drawings

STABLE SOLUTION OF HYALURONATE IN A BALANCED SALT MEDIUM

REFERENCE TO OTHER APPLICATIONS

This application is continuation of application Ser. No. 07/798,835, filed Nov. 25, 1991, abandoned, which is a continuation of application Ser. No. 07/542,389, filed Jun. 23, 1990, abandoned, which is a continuation-in-part of application Ser. No. 07/384,530 filed Jul. 24, 1989, abandoned.

FIELD OF THE INVENTION

The present invention relates to a stable visco-elastic physiologic balanced salt solution of a hyaluronate salt such as sodium hyaluronate which contains both calcium ion and magnesium ion (but no phosphates) to achieve physiologic compatibility.

BACKGROUND OF THE INVENTION

Over the last 20 years there has been a growing awareness of the importance of the use of ionically and osmotically balanced irrigation solutions during intra-ocular surgeries. Originally, all that was available for this purpose was simple sterile saline. While saline was useful as an irrigating solution it was subsequently recognized that the lack of proper salt balance was damaging to the intra-ocular tissues. Over the years different formulations for irrigating solutions had been developed in an attempt to provide more physiologically compatible solutions.

A big advance from simple saline solution was the introduction of phosphate buffered solutions which provided both osmotic balance and pH control. While phosphate buffered saline solutions represented a major step towards less toxic irrigation fluids, they were not completely physiologic and thus produced some cytotoxic effects since they did not contain the requisite balance of salts.

Phosphate buffered saline was soon replaced by balanced salt solutions which were both ionically and osmotically balanced. In addition to sodium chloride, these solutions contained potassium chloride, calcium chloride, magnesium chloride, sodium acetate and sodium citrate. Such balanced salt solutions were judged to be more physiologically compatible with ocular tissue than simple saline or phosphate buffered saline solutions since they contained the essential ions for normal cell metabolism. Various publications in the medical literature have demonstrated the superiority of balanced salt formulations over simple saline or phosphate buffered saline solutions, such as:

1. Edelhauser, H. F., Van Horn, D. L., Hyndiuk, R. A., Schultz, R. O., "Intraocular Irrigating Solutions: Their Effect on the Corneal Endothelium," Arch. Ophthalmol., 93: 648, 1975.
2. Edelhauser, H. F., Van Horn, D. L., Schultz, R. O., Hyndiuk, R. A., "Comparative Toxicity of Intraocular Irrigating Solutions on the Corneal Endothelium", Am. J. Ophthalmol., 81: 473, 1976.
3. Moorhead, L. C., Redburn, D. A., Merritt, J., Garcia, C. A., "The Effects of Intravitreal Irrigation During Vitrectomy on the Electroretinogram," Am. J. Ophthalmol., 88: 239, 1979.

In the development of visco-elastic hyaluronate formulations as medical devices for ophthalmic surgical procedures, it is important that they contain a physiologic balance of salt to minimize toxicity. Although the importance of such a physiologically balanced visco-elastic formulation is well recognized among the ophthalmic community, as of yet none of the commercially available hyaluronate products provide complete physiologic balanced formulations. Dr. James McCulley in Ocular Surgery News, August, 1987, summarizes the importance of physiologic balanced media as follows:

"The cells require electrolytes. If these electrolytes are not present, one start[s] to see toxicity or apparent toxicity and cellular changes. The absence of calcium caused by viscoelastic substances is a major potential problem.

'All of the currently available viscoelastics are made in calcium-free solvents. That apparently is necessary because of the stability of the viscoelastic preparations. If calcium is present in the formulation then it is apparently difficult to maintain the substances in solution, so calcium is removed.

'We're facing a situation where not only calcium, but magnesium and other critical ions are not present. The cells can do fine without nutrients for a short period, but they don't do well without the ions."

Three commercially available hyaluronates for use in ophthalmic surgery are as follows:

a. Healon—each ml of Bealon contains 10 mg of sodium hyaluronate, 8.5 mg of sodium chloride, 0.28 mg of disodium dihydrogen phosphate dihydrate, 0.04 mg of sodium dihydrogen phosphate hydrate and q.s. water for injection USP.

Denlinger, J. L., et al., "Replacement of the Liquid Vitreus with Sodium Hyaluronate in Monkeys," Exp. Eye Res. (1980) 31, 81–99, 101–117, disclose that Healon contains sodium hyaluronate (10±1 mg/ml) "dissolved in a physiological balanced salt solution" (0.145 mg/ml NaCl, 0.34 mg/ml $NaH_2PO_4$; and 1.5 mg/ml $Na_2HPO_4$; pH=7.2±0.2). The term "balanced salt solution" thus refers to an isotonic saline buffered with phosphate.

b. Amvisc—each ml of Amvisc contains 10 mg of sodium hyaluronate adjusted to yield approximately 40,000 centistokes, 9.0 mg of sodium chloride and sterile water for injection USPQS.

c. Viscoat—each 1 ml of Viscoat solution contains not more than 40 mg of sodium chondroitin sulfate, 30 mg sodium hyaluronate, 0.45 mg sodium dihydrogen phosphate hydrate, 2.00 mg disodium hydrogen phosphate, 4.3 mg sodium chloride (with water for injection USP grade, qs).

None of these three products contained the essential ions, in particular magnesium and calcium, which are judged critical for physiologic compatibility. Without these essential ions there can be significant cytotoxicity to the corneal endothelium (corneal cells).

There is available a balanced salt solution marketed by Alcon Labs which is a physiologic irrigation solution for use during various surgical procedures of the eye, ear, nose and/or throat and is listed in the 1988 PDR for ophthalmology as:

BSS is a sterile physiological balanced salt solution of sodium chloride (NaCl), potassium chloride (KCl), calcium chloride ($CaCl_2.2H_2O$), magnesium chloride ($MgCl_2.6H_2O$), sodium acetate ($C_2H_3NaO_2.3H_2O$), and sodium citrate dihydrate ($C_6H_5Na_3O_7.2H_2O$). BSS is isotonic to the tissues of the eyes. It is a lint-free solution containing essential ions for normal cell metabolism. Each ml contains sodium chloride 0.64%, potassium chloride 0.075%, calcium chloride 0.048%, magnesium chloride 0.03%, sodium acetate 0.39%, sodium citrate 0.17%, sodium hydroxide and/or hydrochloric acid (to adjust pH), and water for injection.

The above % may be converted to mg/ml by multiplying each by 10.

The above balanced salt solution has never been used or suggested for use with sodium hyaluronate.

Until now, where it has been attempted to prepare sodium hyaluronate in a balanced salt solution containing calcium ion and magnesium ion, it has been found that the sodium hyaluronate solution was not stable.

DESCRIPTION OF THE INVENTION

In accordance with the present invention, a sterile, stable, isotonic, visco-elastic, non-toxic, physiologic, osmotically balanced salt solution of a hyaluronate salt is provided, in which the hyaluronate salt remains in solution, which contains a hyaluronate salt, such as sodium hyaluronate, sodium ion, chloride ion, potassium ion, calcium ion, magnesium ion, acetate ion, citrate ion and water, at a pH of about 7.3±0.3.

The sodium ion, potassium ion, calcium ion and magnesium ion will be preferably present as sodium chloride, potassium chloride, calcium chloride and magnesium chloride, respectively, while the acetate and citrate will preferably be present as sodium acetate and sodium citrate, respectively. However, these ions may take the form of other salts in lieu of or in addition to the above salts, such as potassium citrate, sodium citrate, calcium citrate, potassium acetate, magnesium acetate, magnesium citrate and the like, provided that the concentration of Na ion, K ion, Ca ion, Mg ion, and citrate are within the teachings of the present invention as defined herein.

For each ml of the balanced salt solution of the invention, the sodium hyaluronate employed will have a molecular weight within the range of from about $0.2 \times 10^6$ to about $10.0 \times 10^6$, and preferably from about $0.25 \times 10^6$ to about $4.0 \times 10^6$, and is present in an amount within the range of from about 0.1% to about 5% by weight, and preferably from about 1.0% to about 3.0% by weight. Other forms of sodium hyaluronate such as those treated with cross linking agents to increase molecular weight may also be employed.

The other ions which make up the balanced salt solution expressed in millimolar concentration ($10^{-3}$ moles/liter) are as follows:

Sodium ($Na^+$) will be present in a concentration range from about 80 mM to about 185 mM and preferably from about 90 mM to about 110 mM.

When combined with sodium hyaluronate, the total sodium concentration of the invention will be in a range from about 120 mM to about 195 mM and preferably from about 130 mM to about 185 mM.

Chloride ($Cl^-$) will be present in a concentration range from about 59 mM to about 89 mM and preferably from about 69 mM to about 79 mM.

Potassium ($K^+$) will be present in a concentration range from about 8.0 mM to about 12.0 mM and preferably from about 9.6 mM to about 10.5 mM.

Calcium ($Ca^{++}$) will be present in a concentration range from about 2.6 mM to about 3.9 mM and preferably from about 3.1 mM to about 3.4 mM.

Magnesium ($Mg^{++}$) will be present in a concentration range from about 1.2 mM to about 1.8 mM and preferably from about 1.4 mM to about 1.6 mM.

Acetate will be present in a concentration range from about 23 mM to about 34 mM and preferably from about 26 mM to about 31 mM.

Citrate will be present in a concentration range from about 4.6 mM to about 6.9 mM and preferably from about 5.1 mM to about 6.5 mM.

The pH of the solution is adjusted to from about 7.0 to about 7.6 and preferably from about 7.2 to about 7.4 with hydrochloric acid or sodium hydroxide as necessary.

The balanced salt solution may also contain other conventional ingredients used in eye irrigating solutions, such as bicarbonate, dextrose and glutathione disulfide, preservatives and the like.

A preferred visco-elastic physiologic balanced salt solution will have the following composition which yields the appropriate ionic concentration.

Each 1 ml of a 30 mg sodium hyaluronate solution will contain:

| | |
|---|---|
| Na hyaluronate | 30 mg |
| NaCl | 3 to 3.4 mg |
| KCl | 0.72 to 0.78 mg |
| $CaCl_2 \cdot 2H_2O$ | 0.46 to 0.5 mg |
| $MgCl_2 \cdot 6H_2O$ | 0.28 to 0.32 mg |
| Na acetate $\cdot 3H_2O$ | 3.6 to 4.1 mg |
| $Na_3$ citrate $\cdot 2H_2O$ | 1.5 to 1.9 mg |
| $H_2O$ | qs 1 ml. |

In another preferred composition, each 1 ml of a 30 mg sodium hyaluronate solution will contain:

| | |
|---|---|
| Na hyaluronate | 30 mg |
| NaCl | 4.3 to 4.7 mg |
| $Na_3$ citrate | 1.3 to 1.7 mg |
| Na acetate | 0.6 to 0.9 mg |
| K acetate | 0.6 to 1.2 mg |
| Mg (acetate)$_2 \cdot 4H_2O$ | 0.2 to 0.4 mg |
| Ca (acetate)$_2 \cdot 2H_2O$ | 0.4 to 0.8 mg |

The above compositions give the following concentrations:

| | | |
|---|---|---|
| Hyaluronate | 3.0% | |
| $Na^+$ | 167.9-182.5 | mM |
| $Cl^-$ | 69.9-78.2 | mM |
| $K^+$ | 9.6-10 | mM |
| $Ca^{++}$ | 3.1-3.4 | mM |
| $Mg^{++}$ | 1.4-1.6 | mM |
| Acetate | 26.5-30.1 | mM |
| Citrate | 5.1-6.5 | mM |

Sterility of the invention can be obtained by either aseptic formulation using sterile salts and sterile water, or post formulation sterilization of the mixture.

It will be appreciated that physiologic balance of the solutions of the invention may be maintained even if less (or more) concentrated hyaluronate solutions are formulated by increasing (or decreasing) the sodium chloride content to offset the reduction (or increase) in sodium from the lesser (or greater) amounts of hyaluronate.

Other salts of hyaluronate such as calcium, magnesium or potassium could be used as long as the final concentration of all salts in solution is within the scope of the invention.

The physiologic visco-elastic balanced salt solution of the invention may be easily formulated by mixing the above ingredients in appropriate amounts of sterile water.

The following Examples represent preferred embodiments of the present invention.

EXAMPLE 1

A visco-elastic ophthalmic device for use during eye surgery having the following composition was prepared by simply mixing the following ingredients.

|  | mg/ml |
| --- | --- |
| Na Hyaluronate (average MW about 400,000) | 30.00 |
| NaCl | 3.20 |
| KCl | 0.75 |
| $CaCl_2 \cdot 2H_2O$ | 0.48 |
| $MgCl_2 \cdot 6H_2O$ | 0.30 |
| Na acetate $\cdot 3H_2O$ | 3.90 |
| $Na_3$ citrate $\cdot 2H_2O$ | 1.70 |
| $H_2O$ for injection USP | qs to 1 ml. |

The above formulation gives the following concentration:

|  | millimolar (mM) |
| --- | --- |
| $Na^+$ | 175.57 |
| $Cl^-$ | 74.30 |
| $K^+$ | 10.06 |
| $Ca^{++}$ | 3.27 |
| $Mg^{++}$ | 1.48 |
| Acetate | 28.66 |
| Citrate | 5.78 |
| Hyaluronate | 42.86μM |

The above solution of sodium hyaluronate is a stable non-toxic isotonic and osmotically balanced salt solution which may be employed as a visco-elastic ophthalmic device for use during eye surgery.

EXAMPLE 2

A visco-elastic ophthalmic device for use during eye surgery having the following composition is prepared by simply mixing the following ingredients.

|  | mg/ml |
| --- | --- |
| Na Hyaluronate (average MW about 400,000) | 30.00 |
| NaCl | 4.58 |
| K acetate | 0.99 |
| Ca (acetate)$_2$ $\cdot 2H_2O$ | 0.63 |
| Mg (acetate)$_2$ $\cdot 4H_2O$ | 0.32 |
| Na acetate | 0.75 |
| $Na_3$ citrate | 1.49 |
| $H_2O$ for injection USP | qs to 1 ml. |

The above formulation gives the following concentration:

|  | millimolar (mM) |
| --- | --- |
| $Na^+$ | 179.67 |
| $Cl^-$ | 78.29 |
| $K^+$ | 10.09 |
| $Ca^{++}$ | 3.24 |
| $Mg^{++}$ | 1.48 |
| Citrate | 5.78 |
| Acetate | 28.66 |
| Hyaluronate | 42.86μM |

The above solution of sodium hyaluronate is a stable non-toxic isotonic and osmotically balanced salt solution which may be employed as a visco-elastic ophthalmic device for use during eye surgery.

What is claimed is:

1. A physiological visco-elastic formulation consisting of sodium hyaluronate in an amount in the range of about 0.1% to about 5% by weight in a balanced salt aqueous solution consisting of calcium ions present in a concentration in the range of about 2.6 mM to about 3.9 mM, magnesium ions present in a concentration in the range of about 1.2 mM to about 1.8 mM, potassium ions, chloride ions, acetate ions, citrate ions and sodium ions, other than sodium present as sodium hyaluronate, present in a concentration in the range of about 90 mM to about 110 mM, said formulation being ionically and osmotically balanced and being free of phosphates.

2. A physiological visco-elastic formulation consisting of sodium hyaluronate in an amount in the range of about 0.1% to about 5% by weight in an osmotically balanced salt aqueous solution consisting of chloride ions in a concentration in the range of about 59 mM to about 89 mM, potassium ions in a concentration in the range of about 8 mM to about 12 mM, calcium ions in a concentration in the range of about 2.6 mM to about 3.9 mM, magnesium ions in a concentration in the range of about 1.2 mM to about 1.8 mM, acetate ions in a concentration in the range of about 23 mM to about 34 mM, citrate ions in a concentration in the range of about 4.6 mM to about 6.9 mM, and sodium ions, other than sodium present as sodium hyaluronate, present in a concentration in the range of about 90 mM to about 110 mM, said formulation being free of phosphates.

3. The formulation as defined in claim 2 including sodium chloride, potassium chloride, calcium chloride, magnesium chloride, sodium acetate, sodium citrate and water.

4. The formulation as defined in claim 2 including sodium chloride, sodium acetate, potassium acetate, magnesium acetate and calcium acetate and water.

5. The formulation as defined in claim 2 wherein the sodium hyaluronate has a molecular weight of within the range of from about $0.2 \times 10^6$ to about $10 \times 10^6$, and said formulation is tonically and osmotically balanced.

6. The formulation as defined in claim 2 having a pH within the range of from about 7 to about 7.6.

7. The formulation as defined in claim 3 having the following composition:

| Na hyaluronate | 30 mg |
| --- | --- |
| NaCl | 3-3.4 mg |
| KCl | 0.72 to 0.78 mg |
| $CaCl_2 \cdot 2H_2O$ | 0.46 to 0.5 mg |
| $MgCl_2 \cdot 6H_2O$ | 0.28 to 0.32 mg |
| Na acetate $\cdot 3H_2O$ | 3.6 to 4.1 mg |
| $Na_3$ citrate $\cdot 2H_2O$ | 1.5 to 1.9 mg |
| $H_2O$ for injection USP | qs 1 ml. |

8. The formulation as defined in claim 3 having the following composition:

|  | mg |
|---|---|
| Na hyaluronate (average MW about 400,000) | 30 |
| NaCl | 3.2 |
| KCl | 0.75 |
| $CaCl_2 \cdot 2H_2O$ | 0.48 |
| $MgCl_2 \cdot 6H_2O$ | 0.3 |
| Na acetate $\cdot 3H_2O$ | 3.9 |
| $Na_3$ citrate $\cdot 2H_2O$ | 1.7 |
| $H_2O$ for injection USP | qs to 1 ml. |

9. The formulation as defined in claim 4 having the following composition:

| Na hyaluronate | 30 mg |
|---|---|
| NaCl | 4.3 to 4.7 mg |
| $Na_3$ citrate | 1.3 to 1.7 mg |
| Na acetate | 0.6 to 0.9 mg |
| K acetate | 0.6 to 1.2 mg |
| Mg (acetate)$_2 \cdot 4H_2O$ | 0.2 to 0.4 mg |
| Ca (acetate)$_2 \cdot 2H_2O$ | 0.4 to 0.8 mg |
| $H_2O$ for injection USP | qs to 1 ml |

10. The formulation as defined in claim 4 having the following composition:

| Na hyaluronate | 30 mg |
|---|---|
| NaCl | 4.58 mg |
| $Na_3$ citrate | 1.49 mg |
| Na acetate | 0.75 mg |
| K acetate | .99 mg |
| Mg (acetate)$_2 \cdot 4H_2O$ | .32 mg |
| Ca (acetate)$_2 \cdot 2H_2O$ | .63 mg |
| $H_2O$ for injection USP | qs to 1 ml |

11. The formulation as defined in claim 1 wherein the hyaluronate salt is a magnesium, calcium or potassium salt of hyaluronic acid.

12. The formulation as defined in claim 1 which is free of sulfates.

13. The formulation as defined in claim 1 wherein chloride ions are present in a concentration in the range of about 59 mM to about 89 mM.

14. The formulation as defined in claim 1 wherein potassium ions are present in a concentration in the range of about 9.6 mM to about 10.5 mM.

15. The formulation as defined in claim 1 wherein calcium ions are present in a concentration in the range of about 3.1 mM to about 3.4 mM.

16. The formulation as defined in claim 1 wherein acetate ions are present in a concentration in the range of about 23 mM to about 34 mM.

17. The formulation as defined in claim 2 which is free of sulfates.

18. In a method of performing surgery on an eye including employing a visco-elastic material during the performance of said surgery, the improvement which comprises utilizing the formulation of claim 1 as said visco-elastic material.

19. In a method of performing surgery on an eye including employing a visco-elastic material during the performance of said surgery, the improvement which comprises utilizing the formulation of claim 2 as said visco-elastic material.

* * * * *

UNITED STATES PATENT AND TRADEMARK OFFICE
CERTIFICATE OF CORRECTION

PATENT NO.    : 6,271,216 B1
DATED         : August 7, 2001
INVENTOR(S)   : Mello et al.

It is certified that error appears in the above-identified patent and that said Letters Patent is hereby corrected as shown below:

Column 6,
Line 50, "tonically" should read -- ionically --.

Signed and Sealed this

First Day of July, 2003

JAMES E. ROGAN
*Director of the United States Patent and Trademark Office*